US 6,589,922 B1

(12) United States Patent
Dow et al.

(10) Patent No.: US 6,589,922 B1
(45) Date of Patent: Jul. 8, 2003

(54) SKIN CLEANSER COMPRISING A STEARETH, POLOXAMER, AND A GLYCERYL MONOESTER

(75) Inventors: Gordon J. Dow, Santa Rosa, CA (US); Kevin Bean, Santa Rosa, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 0 days.

(21) Appl. No.: 09/802,047

(22) Filed: Mar. 8, 2001

(51) Int. Cl.$^7$ .............................................. C11D 1/825
(52) U.S. Cl. ..................... 510/130; 510/135; 510/136; 510/155; 510/421; 510/432; 510/437; 510/491
(58) Field of Search ................................. 510/130, 135, 510/136, 155, 421, 432, 437, 491

(56) References Cited

U.S. PATENT DOCUMENTS

| | | | | |
|---|---|---|---|---|
| 3,944,506 A | * | 3/1976 | Hramchenko et al. | 252/526 |
| 4,382,919 A | * | 5/1983 | Alonso et al. | 424/65 |
| 4,517,176 A | * | 5/1985 | Felger | 424/47 |
| 4,976,953 A | * | 12/1990 | Orr et al. | 424/47 |
| 5,011,681 A | * | 4/1991 | Ciotti et al. | 424/81 |
| 5,030,374 A | * | 7/1991 | Tranner | 252/90 |
| 5,434,144 A | * | 7/1995 | Kasting et al. | 514/76 |
| 5,569,461 A | * | 10/1996 | Andrews | 424/405 |
| 5,569,651 A | * | 10/1996 | Garrison et al. | 514/159 |
| 5,605,933 A | * | 2/1997 | Duffy et al. | 514/557 |
| 5,612,347 A | * | 3/1997 | Cauwenbergh et al. | 514/259 |
| 5,674,511 A | | 10/1997 | Kacher et al. | |
| 5,719,126 A | * | 2/1998 | Nordlund et al. | 514/12 |
| 5,780,060 A | * | 7/1998 | Levy et al. | 424/489 |
| 5,780,504 A | * | 7/1998 | Ptchelintsev | 514/474 |
| 5,821,237 A | * | 10/1998 | Bissett et al. | 514/75 |
| 5,885,596 A | * | 3/1999 | Parab | 424/401 |
| 6,150,313 A | * | 11/2000 | Harmalker et al. | 510/130 |
| 6,214,318 B1 | * | 4/2001 | Osipow et al. | 424/45 |

OTHER PUBLICATIONS

Physicians Desk Reference, "Cetaphil®—Gentle Skin Cleanser", p. 972 (1994).
Condea Product Information, "Imwitor" Glyceryl Monolaurate Ester, (1999).
Domingo et al., "Influence of Highly Ethoxylated Nonionic Surfactants on the Properties of Sodium Lauryl Ether Sulfates", (Abstract) 13th IFSCC Congress, Buenos Aires, Argentina (1984).
BASF, "The Wonderful World of Pluronic Polyols", BASF Wyandotte Corporation (1973).

* cited by examiner

*Primary Examiner*—Charles Boyer
(74) *Attorney, Agent, or Firm*—Howard Eisenberg, Esq.

(57) ABSTRACT

A non-irritating skin cleanser that contains water, a non-ionic surfactant, and a glyceryl monoester of a fatty acid. The skin cleanser is especially useful for cleansing irritated, diseased, damaged, or sensitive skin. The cleanser is especially useful for cleansing hands.

74 Claims, No Drawings

SKIN CLEANSER COMPRISING A STEARETH, POLOXAMER, AND A GLYCERYL MONOESTER

FIELD OF THE INVENTION

The invention pertains to the field of cleansers for skin, and most particularly to skin cleansers that may be used on sensitive, damaged, diseased, or irritated skin.

BACKGROUND OF THE INVENTION

Cleansing products represent one of the major risk factors for occupational dermatitis, particularly hand dermatitis. Chronic irritant contact dermatitis is due in many cases to repeated exposure to weak irritants, such as present in many skin cleansers. Also, certain endogenous skin diseases, such as atopic dermatitis, are exacerbated by exposure to irritants found in these cleansing products. Additionally, many individuals who have sensitive skin, even without having dermatitis, experience symptoms of irritation, such as redness, stinging, tingling, burning and itching, when using topical cleansing products on intact skin.

The mildness (lack of tendency to cause irritation) of a cleansing product is related to the formulation of the particular detergent or detergents and their concentration in the cleansing product. Also, the risk of chronic irritant dermatitis or exacerbation of endogenous dermatitis increases with increased frequency of washing. This is especially a problem in occupations that require frequent hand washing, such as in workers in the medical and food service fields.

CETAPHIL® Cleanser (Galderma Laboratories, Ft. Worth, Tex.) is recognized as the leading mild skin cleanser and is frequently recommended by physicians for use by patients with atopic dermatitis and hand dermatitis. Even though this product is recognized as being mild, tests have shown that its use results in significant irritation to human skin when evaluated in a patch test. Chronic use of CETAPHIL® or other cleansing products made for skin can perpetuate or worsen a dermatitis, particularly in individuals with sensitive skin.

Therefore, a significant need exists for a milder skin cleanser for individuals with sensitive skin, atopic dermatitis, or latent, incipient or frank hand dermatitis. In addition to being mild, such a hand cleanser should be effective as a cleanser and should moisturize.

SUMMARY OF THE INVENTION

The present invention is a major improvement in mild skin cleansers and in methods of cleansing skin. Although useful in individuals with normal skin, the invention is most useful in those individuals with sensitive skin who are vulnerable to developing skin disorders and those individuals who are currently suffering from such disorders.

In one embodiment, the invention is a composition for cleansing skin, especially for diseased or sensitive skin. The composition is most useful for cleaning the hands, but may also be used to clean the skin on any other part of the body. The composition of the invention is demonstrably less irritating than CETAPHIL® Cleanser in a comparative repeat insult patch test. The composition is stable, cosmetically elegant, well tolerated by users, and cleanses effectively while moisturizing the skin. Compositions of this invention may be safely used for frequent cleansings such as hand washings required of food workers and medical personnel. The composition may also be used to prevent or to treat or manage dermatitis, especially hand dermatitis.

In another embodiment, the invention is a method for cleaning skin, such as the skin of the hands. According to this embodiment, a formulation containing the composition of the invention is applied to the skin. The formulation is then removed from the skin, either with or without water.

In another embodiment, the invention is a method for prevention of dermatitis in individuals susceptible to developing dermatitis, especially of the hands. According to this embodiment, the invention comprises cleansing the skin with a formulation containing the composition of the invention by applying the formulation to the skin and then removing it from the skin.

In another embodiment, the invention is a method for treatment or management of dermatitis, especially hand dermatitis. According to this embodiment, an individual suffering from this condition cleanses his or her skin with a formulation containing the composition of the invention.

In another embodiment, the invention is a method for making a moisturizing skin cleanser. According to this embodiment, the method includes combining one or more non-ionic surfactants with a glyceryl monoester. Preferably, one or more saturated fatty alcohols is also combined with the surfactant and the glyceryl monoester.

DETAILED DESCRIPTION OF THE INVENTION

The composition of the invention is useful as a component of a formulation, or as the entire formulation, that is useful as a skin cleanser, particularly for the hands. The skin cleanser is especially useful for preventing dermatitis in susceptible individuals and in managing and treating individuals suffering from dermatitis, such as atopic dermatitis or hand dermatitis. The cleanser of the invention may be used with or without water during the cleansing process. The water may be used to increase the lather of the cleanser or to rinse the cleanser from the skin of the user. Cleansing without water may be accomplished by massaging the cleanser onto the skin to be cleaned and then wiping any soil and excess cleanser off the skin with a cloth or paper towel or facial tissue.

According to the invention, the composition of the invention contains one or more non-ionic surfactants. Examples of suitable non-ionic surfactants include poloxamers and steareths.

Poloxamers are also known as polyoxyethylene polyoxypropylene block polymers. They are sold under the trade name PLURONIC™ by BASF of Washington, N.J., which markets several grades of PLURONIC™. A preferred poloxamer for the composition of the invention is poloxamer 123, as described in the National Formulary. The BASF name for this poloxamer is PLURONIC L43.

One company that makes steareths is ICI America of Wilmington, Del., where they are sold under the trade name BRIJ™. One preferred steareth for the composition of the invention is BRIJ 72, which is also known as steareth-2. Other names for steareth-2 are PEG-2 Stearyl Ether, Polyoxyethylene (2) Stearyl Ether, and Polyethylene Glycol 100 Stearyl Ether. Other preferred steareths for the composition of the invention are BRIJ 78 and 721, which are also known as steareth-20 and 21, respectively.

Suitable total concentrations of non-ionic surfactant for the composition and formulation of the invention are from about 0.5% to about 10% by weight for poloxamers and/or steareths. A preferred range is from about 1% to about 5%, and a most preferred range from about 1.25% to about 2.5%.

The composition of the invention further contains one or more glyceryl monoesters of a fatty acid, also known as fatty acid monoglycerides. The terms "glyceryl monoester" and "monoglyceride" are used synonymously throughout this specification to in reference to fatty acid esters. It has been discovered that such glyceryl monoesters in accordance with the invention provide unexpected benefits to the compositions of the invention, including physical stabilization and reproducibility of pharmaceutical attributes. The glyceryl monoesters have also unexpectedly been found to contribute to the moisturizing properties and to the mildness of the compositions of the invention. Preferably, the monoester content or purity, also known as the monoglyceride content or purity, of the glyceryl monoester is at least about 50%, although it may be lower if desired, such as between 35% and 50%. Preferably, the fatty acid component of the glyceryl monoester is of fatty acids having a chain length of between C8 to C22, which fatty acids are preferably substantially or entirely saturated.

Suitable total concentrations of glyceryl monoester for the composition and formulation of the invention are from about 0.1% to about 5% by weight. A preferred concentration of glyceryl monoester is from about 0.5% to 2%. The most preferred concentration is about 1%.

A preferred glyceryl monoester is glyceryl monolaurate, sold for example under the trade name IMWITOR 312 (Salol Co., Houston, Tex.). The characteristic monoglyceride purity is about 90% or more. Other technical names for glyceryl monolaurate include glyceryl laurate, 1-monolaurin, monolaurin, glycerin 1-monolaurate, glycerol 1-monolaurate and lauric acid 1-monoglyceride. Another preferred glyceryl monoester is glyceryl monostearate, sold for example under the trade names EMEREST 2400 (Henkel, Hoboken, N.J.) and IMWITOR 191 or IMWITOR 900 (Salol Co., Houston, Tex.). The characteristic monoglyceride purity of IMWITOR 191 is about 90% or more for example, and the purity of IMWITOR 900 is characteristically about 42% to about 50%. Glyceryl monostearate is also known by the following technical names: glyceryl stearate, monostearin, glycerol 1-stearate, and stearic acid 1-monoglyceride. Some commercial formulations of glyceryl monoesters are blended with emulsifiers to make the mixture self-emulsifying. Such materials, such as ARLACEL 165 (ICI Americas, Inc.) are neither required nor preferred for the present invention.

An optional component of the composition of the invention is one or more saturated fatty It alcohols. Preferred saturated fatty alcohols include cetyl and stearyl alcohols. Saturated fatty alcohols can be obtained from various suppliers known to one skilled in the art. The NF grade is preferred for the saturated fatty alcohols. If present, the total concentration of the saturated fatty alcohols in the composition may be from about 0.25% to about 5% by weight. Higher or lower concentrations of saturated fatty alcohols may be used if desired. The preferred amount is about 0.5% to about 4%, and the most preferred amount is from about 1.5% to about 3.5%.

The composition of the invention may further include one or more humectants. Preferred humectants include glycerin and sorbitol. The humectants can be obtained from various suppliers known to one skilled in the art. The USP grade is preferred for glycerin and for sorbitol. If present, the total concentration of the humectant or humectants in the composition may be from about 0.5% to about 15% by weight. Higher or lower concentrations of humectant may be used if desired. The preferred concentration range is from about 2.5% to about 10%, and the most preferred range of concentration is from about 3% to about 5%.

Other optional ingredients may be included in the invention to provide additional properties. For example, the composition may include a preservative to prevent spoilage. Fragrances and odor maskers may also be used. However, fragrances and odor maskers are not preferred because of the potential for irritation and allergic reactions.

Preferably, although not necessarily, the composition of the invention is substantially free of ethylene glycol fatty acid ester. Preferably, although not necessarily, the composition of the invention is substantially free of fatty acid soap.

In preferred embodiments, the composition and formulation of the invention are liquids. Preferably, the invention is a mild, low foaming, aqueous fluid cleanser that is pourable from a bottle or dispensable by a pump or squeeze bottle. Preferably, the liquid cleanser of the invention has a viscosity less than about 17000 centipoise, and most preferably between 7000 and 17000 centipoise. Other physical forms of the invention are also conceived, like a solid or semisolid, such as resembling a bar of soap.

The composition of the invention may be made by combining the ingredients in an aqueous medium and mixing to distribute all the ingredients substantially evenly throughout the aqueous medium. Preferably, the water and the other ingredients are heated to about 70° C. or higher. Preferred methods of making the composition of the invention are described below.

The invention is further described in the following non-limiting examples.

EXAMPLE 1

A mild fluid cleanser for individuals with sensitive skin and for patients with hand dermatitis, atopic dermatitis or other skin disorders. This cleanser is marketed under the trade name LUBREX® GENTLE HAND CLEANSER (Allerderm Laboratories, Petaluma, Calif.).

| Excipients | % w/w |
| --- | --- |
| Stearyl alcohol | 0.5 |
| Cetyl alcohol | 3.0 |
| Poloxamer 123 | 0.4 |
| Glycerin | 2.0 |
| Sorbitol solution (70%) | 2.0 |
| Steareth-21 | 0.8 |
| Steareth-2 | 0.2 |
| Glyceryl monolaurate | 1.0 |
| Benzyl alcohol | 1.2 |
| Purified water | QSAD 100 |

This cleanser may be made according to the following steps.

1. Combine purified water, glycerin, sorbitol solution, and poloxamer 123 in a container, such as a beaker. Mix, such as with a propeller mixer, to blend. Heat to about 70° to 80° C. while mixing to make a water phase.

2. Combine stearyl alcohol, cetyl alcohol, glyceryl monostearate, steareth-21 and steareth-2 in a separate container, such as a beaker. Heat to melt all solids, such as to 70° to 80° C. Stir to blend ingredients to make an oil phase.

3. Add the oil phase to the water phase while hot and while mixing, such as with a propeller or preferably with by rotor-stator homogenizing mixing. Add, preferably immediately, the benzyl alcohol and continue mixing for about 5 to 10 minutes or more.

4. Cool the mixture of step 3 to room temperature, preferably by using a water bath or water jacket, while continuing gentle stirring.

EXAMPLE 2

An alternative mild fluid cleanser for individuals with sensitive skin and for patients with hand dermatitis, atopic dermatitis or other skin disorders in accordance with the invention. This cleanser is an alternative form of LUBREX® GENTLE HAND CLEANSER that differs from that of Example 1 in the type of steareth included.

| Excipients | % w/w |
| --- | --- |
| Stearyl alcohol | 0.5 |
| Cetyl alcohol | 3.0 |
| Poloxamer 123 | 0.4 |
| Glycerin | 2.0 |
| Sorbitol solution (70%) | 2.0 |
| Steareth-20 | 0.8 |
| Steareth-2 | 0.2 |
| Glyceryl monolaurate | 1.0 |
| Benzyl alcohol | 1.2 |
| Purified water | QSAD 100 |

This cleanser may be made by the following steps.

1. Combine purified water, glycerin, sorbitol solution and Poloxamer 123 in a container, such as a beaker. Mix, such as with a propeller mixer, to blend. Heat to about 70° to 80° C. while mixing to make a water phase.

2. Combine stearyl alcohol, cetyl alcohol, glyceryl monostearate, steareth-20 and steareth-2 in a separate container, such as a beaker. Heat to about 70° to 80° C. to melt all solids. Stir to blend ingredients, thus making an oil phase.

3. Add the oil phase to the water phase while hot and while mixing, such as with a propeller or preferably with by rotor-stator homogenizing mixing. Add, preferably immediately, the benzyl alcohol and continue mixing for about 5 to 10 minutes or more.

4. Cool the mixture of step 3 to room temperature, preferably by using a water bath or water jacket, while continuing gentle stirring.

EXAMPLE 3

Typical Parameters for LUBREX® Gentle Hand Cleansers described in Examples 1 and 2 are as follows:

| TEST PARAMETER | METHOD | TYPICAL RESULTS |
| --- | --- | --- |
| 1. Description of product | appearance | Visual Viscous white opaque liquid |
| 2. Viscosity | Brookfield LVT viscometer (Spindle #3 @ 6 rpm @ 25° C. ± 2° C.) | 7,000 to 17,000 centipoise |
| 3. pH | Measure neat with calibrated pH meter at 25° C. | 3.0 to 8.0 |
| 4. Specific Gravity | | 0.97 to 1.00 |

EXAMPLE 4

Prior Art Skin Cleanser

CETAPHIL® Gentle Cleanser is marketed by Galderma Laboratories, Inc., Fort Worth, Tex. CETAPHIL® is the currently best accepted mild cleanser among dermatologists in the United States. The labeling for CETAPHIL® is as follows:

"CETAPHIL® cleanser was formulated for dermatologists as a gentle, non-irritating cleanser for even the most sensitive skin. Unlike soap, CETAPHIL® is completely non-alkaline, non-comedogenic, and fragrance free. Soothes and softens as it cleanses, helping the skin retain needed moisture. Use for face, hands, and the entire body. Also an excellent cleanser for the delicate skin of babies.

CETAPHIL® cleanser is easy to use:

Without Water: Apply a liberal amount to the skin and rub gently. The unique, low lathering formula allows gentle, yet thorough cleansing. Remove excess with a soft cloth, leaving a thin film of CETAPHIL® on the skin. The emollient quality will leave the skin soft and moist.

With Water: Apply to the skin and rub gently. Rinse.

Ingredients: Water, Cetyl Alcohol, Propylene Glycol, Sodium Lauryl Sulfate, Stearyl Alcohol, Methylparaben, Propylparaben, Butylparaben."

EXAMPLE 5

Comparison of the Invention and the Prior Art

A comparative 3-day repeat insult patch test was performed to test the human skin irritation potential of the composition in Example 1 of the present invention in comparison with the prior art cleanser of Example 4.

Finn Chambers® on Scanpor® (Allerderm Laboratories, Petaluma, Calif.) patches with a diameter of 12 mm were filled with approximately 0.07 grams of each test material in duplicate and placed on the back or inner arms of three volunteer test subjects with very sensitive (Fitzpatrick type 1) skin. At 24 and 48 hours, the test materials were removed and reapplied to the same sites. Neither the test subjects nor the evaluators knew the identity of the materials at the test sites. Two independent evaluators made visual irritation assessments at three times, approximately 8, 24 and 48 hours after the third day patch removal.

Irritation was scored on a scale of 0 to 4. A score of 0 indicated no visible reaction and/or erythema. A score of 1 indicated a mild macular erythema reaction. A score of 2 indicated a moderate macular erythema reaction. A score of 3 indicated a strong to severe macular erythema reaction. And a score of 4 indicated the presence of generalized vesicles or eschar formation or severe erythema with edema extending beyond the patch.

The results show the embodiment of the present invention as illustrated in Example 1 to be non-irritating and the CETAPHIL® cleanser of Example 4 to be moderately irritating under the conditions of this patch test. The test data are as follows:

| Test Material | Total Score | Average Score | Irritation Rating |
| --- | --- | --- | --- |
| LUBREX ® Cleanser of Example 1 | 4.2 | 0.1 | None |
| CETAPHIL ® Cleanser of Example 4 | 88.0 | 2.4 | Moderate |

EXAMPLE 6

Stability Studies

The stability of the formulation of Example 1 was evaluated in 8 ounce high density polyethylene bottles at accelerated and at ambient test conditions and found to be commercially stable. During 6 months of accelerated storage at 40° C. and 75% relative humidity, it was found to be stable in all respects. Product appearance was always in compliance with the standard, the pH was always between 3.6 and 3.8, and viscosity results were stable within the range of 11,550 to 12,950 centipoise. During 12 months of storage at room temperature (25° C. and 60% relative humidity), results were also stable in all respects. The product appearance was always in compliance with the standard, the pH was always between 3.6 and 3.8, and viscosity results were stable within the range of 12,000 to 13,000 centipoise.

EXAMPLE 7

Objective Evaluation of the Skin Cleanser of Example 2

An experiment was conducted with the skin cleanser composition of Example 2 in order to obtain in use evaluation of the product for cleansing, tolerability and cosmetic attributes. Sixteen female and fifteen male volunteers, ages 24 to 63, used the cleanser of Example 2 to wash their hands and average of 3 times (range 1 to 20 times). Completed questionnaires revealed that 97% of the test subjects reported that LUBREX® Cleanser cleansed their hands "very well" or "good." Subjects typically reported that the product left their hands feeling "refreshed," "soft," and "moisturized," and that the product was easy to use. The questionnaire collected data rating sensations of sensitivity and irritation including tingling, burning, or stinging as none, slight, moderate or extreme. Each of the 31 subjects reported "none" for tingling, burning and stinging.

EXAMPLE 8

Subjective Assessment of the Skin Cleanser of Example 2

Users have had good results and have been very pleased with LUBREX® Cleanser, as described in Example 2.

Sarah T. from Boston reported that she was very allergic to traditional soaps and recently found that she was allergic to sodium laureth sulfate, which is an ingredient found in many soap-free cleansing products. She tried LUBREX® Cleanser of Example 2 by first doing a patch test which was negative as to irritation. She reported using the product for her face, hands and even hair with no ill effects.

Michele P. of California had a rash on her hands for 20 years and used steroid creams but the rash always recurred. After using LUBREX® Cleanser as described in Example 2 exclusively to wash her hands, the rash did not return. She said that she believes that something in all soaps and creams must have been an irritation to her skin. She said that LUBREX® Cleanser is "remarkable."

EXAMPLE 9

An alternative mild fluid cleanser for individuals with sensitive skin and for patients with hand dermatitis, atopic dermatitis or other skin disorders in accordance with the invention. This cleanser is an alternative form of LUBREX® GENTLE HAND CLEANSER that differs from that of Example 1 in the inclusion of several optional ingredients.

| Excipients | % w/w |
|---|---|
| Stearyl alcohol | 0.5 |
| Cetyl alcohol | 3.0 |
| Poloxamer 123 | 0.4 |
| Glycerin | 2.0 |
| Sorbitol solution (70%) | 2.0 |
| Steareth-21 | 0.8 |
| Steareth-2 | 0.2 |
| Glyceryl monolaurate | 1.0 |
| Sodium salicylate | 0.3 |
| Phytosphingosine | 0.042 |
| Disodium edetate | 0.025 |
| Purified water | QSAD 100 |

This cleanser may be made according to the following steps.

1. Combine purified water, glycerin, sorbitol solution, disodium edetate, sodium salicylate, and poloxamer 123 in a container, such as a beaker. Mix, such as with a propeller mixer, to blend. Heat to about 70° while mixing to make a water phase.

2. Combine stearyl alcohol, cetyl alcohol, glyceryl monostearate, phytosphingosine, steareth-21 and steareth-2 in a separate container, such as a beaker. Heat to 70° C. to melt all solids. Stir to blend ingredients to make an oil phase.

3. Add the oil phase to the water phase while hot and while mixing, such as with a propeller or preferably with by rotor-stator homogenizing mixing. Continue mixing for about 5 to 10 minutes or more.

4. Cool the mixture of step 3 to room temperature, preferably by using a water bath or waterjacket, while continuing gentle stirring.

EXAMPLE 10

Hand Washing Efficiency of the Cleanser of Example 9

The LUBREX® cleanser described in Example 9 was tested by two individuals for hand washing efficiency. One male and one female subject purposely soiled both of their hands to simulate gardening activity without gloves. Ordinary outdoor mud was rubbed thoroughly into the palms and allowed to dry for 5 minutes.

Then about 5 ml of the cleanser of Example 9 was applied to the palm of one hand and then rubbed gently over all surfaces of both hands in the manner used in ordinary hand washing. A water-free cleansing method was employed. That is, no water was used to facilitate washing or rinsing. The cleanser readily picked up the dirt as evidenced by the discoloration of the initial white foam of the cleanser during the cleaning process. After about two minutes of washing, the residual cleanser and entrapped dirt was removed by wiping with paper toweling. The dried hands were checked for cleanliness by observation and by rubbing the hands with a clean, damp white cloth. After using the composition in Example 9 both subjects reported clean hands by both visual and damp cloth test.

While the foregoing has presented specific embodiments of the present invention, it is to be understood that these embodiments have been presented by way of example only. It is expected that others skilled in the art will perceive variations which, while varying from the foregoing, do not depart from the spirit and scope of the invention herein described and claimed. For example, the invention encom-

What is claimed is:

1. A non-irritating skin cleanser comprising a poloxamer, and a steareth, and a glyceryl monoester of a fatty acid, wherein the total concentration of the poloxamer and the steareth in the cleanser is between 0.5% and 10% w/w and the concentration of the glyceryl monoester is between 0.1% and 5% w/w.

2. The skin cleanser of claim 1 which is free of propylene glycol.

3. The skin cleanser of claim 1 which is free of sodium lauryl sulfate.

4. The skin cleanser of claim 2 which is free of sodium lauryl sulfate.

5. The skin cleanser of claim 1 wherein the glyceryl monoester of a fatty acid is glyceryl monolaurate or glyceryl monostearate.

6. The skin cleanser of claim 5 wherein the glyceryl monoester is glyceryl monolaurate.

7. The skin cleanser of claim 1 which further comprises sorbitol.

8. The skin cleanser of claim 2 which further comprises sorbitol.

9. The skin cleanser of claim 3 which further comprises sorbitol.

10. The skin cleanser of claim 1 wherein the poloxamer is Poloxamer 123.

11. The skin cleanser of claim 1 wherein the steareth is selected from the group consisting of steareth-2, steareth-21, and steareth 20.

12. The skin cleanser of claim 1 which further comprises a saturated fatty alcohol.

13. The skin cleanser of claim 12 wherein the saturated fatty alcohol is selected from the group consisting of cetyl alcohol and stearyl alcohol.

14. The skin cleanser of claim 13 which comprises the following ingredients:
cetyl alcohol, stearyl alcohol, glyceryl monolaurate, steareth-2, poloxamer 123, and either or both of steareth-21 and steareth-20, and which comprises glycerin and sorbitol.

15. The skin cleanser of claim 14 which comprises the following ingredients in the following concentrations w/w:

| | |
|---|---|
| cetyl alcohol | 3.0, |
| stearyl alcohol | 0.5, |
| poloxamer 123 | 0.4, |
| glycerin | 2.0, |
| 70% sorbitol solution | 2.0, |
| steareth-21 or steareth-20 | 0.8, |
| steareth-2 | 0.2, |
| glyceryl monolaurate | 1.0, and |
| water | QSAD 100. |

16. A method for making a non-irritating skin cleanser comprising combining water, poloxamer, a steareth, and a glyceryl monoester of a fatty acid, wherein the total concentration of the poloxamer and the steareth that is combined to make the cleanser is between 0.5% and 10% w/w and the concentration of the glyceryl monoester that is combined to make the cleanser is between 0.1% and 5% w/w and mixing to obtain a substantially homogeneous dispersion of the poloxamer, steareth, and glyceryl monoester in the water.

17. The method of claim 16 which comprises combining sorbitol in the dispersion.

18. The method of claim 16 wherein propylene glycol is not combined in the dispersion.

19. The method of claim 16 wherein sodium lauryl sulfate is not combined in the dispersion.

20. The method of claim 19 wherein neither propylene glycol nor sodium lauryl sulfate is combined in the dispersion.

21. The method of claim 16 wherein the glyceryl monoester is glyceryl monolaurate or glyceryl monostearate.

22. The method of claim 21 wherein the glyceryl monoester is glyceryl monolaurate.

23. The method of claim 16 which further comprises combining a saturated fatty alcohol in the dispersion.

24. The method of claim 23 wherein the saturated fatty alcohol is selected from the group consisting of cetyl alcohol and stearyl alcohol.

25. The method of claim 24 comprises combining the following ingredients:
cetyl alcohol, stearyl alcohol, glyceryl monolaurate, steareth-2, poloxamer 123, and either or both of steareth-21 and steareth-20, and further combining glycerin and sorbitol with said ingredients.

26. The method of claim 25 which comprises combining the following ingredients in the following concentrations w/w:

| | |
|---|---|
| cetyl alcohol | 3.0, |
| stearyl alcohol | 0.5, |
| poloxamer 123 | 0.4, |
| glycerin | 2.0, |
| 70% soybitol solution | 2.0, |
| steareth-21 or steareth-20 | 0.8, |
| steareth-2 | 0.2, |
| glyceryl monolaurate | 1.0, and |
| water | QSAD 100. |

27. A skin cleanser made by the method of claim 16.
28. A skin cleanser made by the method of claim 17.
29. A skin cleanser made by the method of claim 18.
30. A skin cleanser made by the method of claim 19.
31. A skin cleanser made by the method of claim 20.
32. A skin cleanser made by the method of claim 21.
33. A skin cleanser made by the method of claim 22.
34. A skin cleanser made by the method of claim 23.
35. A skin cleanser made by the method of claim 24.
36. A skin cleanser made by the method of claim 25.
37. A skin cleanser made by the method of claim 26.

38. A method for cleansing the skin without irritating the skin comprising applying to the surface of the skin a cleanser comprising a poloxamer, a glyceryl monoester of a fatty acid, and a steareth, and then removing the cleanser from the skin wherein the total concentration of the poloxamer and the steareth in the cleanser is between 0.5% and 10% w/w and the concentration of the glyceryl monoester is between 0.1% and 5% w/w.

39. The method of claim 38 wherein the cleanser is free of propylene glycol.

40. The method of claim 38 wherein the cleanser is free of sodium lauryl sulfate.

41. The method of claim 39 wherein the cleanser is free of sodium lauryl sulfate.

42. The method of claim 38 wherein the glyceryl monoester of a fatty acid is glyceryl monolaurate or glyceryl monostearate.

43. The method of claim 42 wherein the glyceryl monoester is glyceryl monolaurate.

44. The method of claim 38 wherein the cleanser further comprises sorbitol.

45. The method of claim 39 wherein the cleanser further comprises sorbitol.

46. The method of claim 40 wherein the cleanser further comprises sorbitol.

47. The method of claim 41 wherein the cleanser further comprises sorbitol.

48. The method of claim 38 wherein the poloxamer is Poloxamer 123.

49. The method of claim 38 wherein the steareth is selected from the group consisting of steareth-2, steareth-21, and steareth 20.

50. The method of claim 38 wherein the cleanser further comprises a saturated fatty alcohol.

51. The method of claim 50 wherein the saturated fatty alcohol is selected from the group consisting of cetyl alcohol and stearyl alcohol.

52. The method of claim 51 wherein the cleanser comprises the following ingredients:

cetyl alcohol, stearyl alcohol, glyceryl monolaurate, steareth-2, poloxamer 123, and either or both of steareth-21 and steareth-20, and wherein the cleanser further comprises glycerin and sorbitol.

53. The method of claim 52 wherein the cleanser comprises the following ingredients in the following concentrations w/w:

| | |
|---|---|
| cetyl alcohol | 3.0, |
| stearyl alcohol | 0.5, |
| poloxamer 123 | 0.4, |
| glycerin | 2.0, |
| 70% sorbitol solution | 2.0, |
| steareth-21 or steareth-20 | 0.8, |
| steareth-2 | 0.2, |
| glyceryl monolaurate | 1.0, and |
| water | QSAD 100. |

54. The skin cleanser of claim 1 wherein the total concentration of the poloxamer and the steareth is between about 1% and about 5%.

55. The skin cleanser of claim 1 wherein the total concentration of the poloxamer and the steareth is between about 1.25% and about 2.5%.

56. The skin cleanser of claim 1 wherein the concentration of the glyceryl monoester is between 0.5% and 2%.

57. The skin cleanser of claim 54 wherein the concentration of the glyceryl monoester is between about 0.5% and 2%.

58. The skin cleanser of claim 55 wherein the concentration of the glyceryl monoester is between about 0.5% and 2%.

59. The method of claim 16 wherein the total concentration of the poloxamer and the steareth is between about 1% and about 5%.

60. The method of claim 16 wherein the total concentration of the poloxamer and the steareth is between about 1.25% and about 2.5%.

61. The method of claim 16 wherein the concentration of the glyceryl monoester is between 0.5% and 2%.

62. The method of claim 59 wherein the concentration of the glyceryl monoester is between about 0.5% and 2%.

63. The method of claim 60 wherein the concentration of the glyceryl monoester is between about 0.5% and 2%.

64. A skin cleanser made by the method of claim 16.

65. A skin cleanser made by the method of claim 59.

66. A skin cleanser made by the method of claim 60.

67. A skin cleanser made by the method of claim 61.

68. A skin cleanser made by the method of claim 62.

69. A skin cleanser made by the method of claim 63.

70. The method of claim 38 wherein the total concentration of the poloxamer and the steareth is between about 1% and about 5%.

71. The method of claim 38 wherein the total concentration of the poloxamer and the steareth is between about 1.25% and about 2.5%.

72. The method of claim 38 wherein the concentration of the glyceryl monoester is between 0.5% and 2%.

73. The method of claim 72 wherein the concentration of the glyceryl monoester is between about 0.5% and 2%.

74. The method of claim 73 wherein the concentration of the glyceryl monoester is between about 0.5% and 2%.

* * * * *